(12) United States Patent
Smith et al.

(10) Patent No.: US 6,544,200 B1
(45) Date of Patent: Apr. 8, 2003

(54) ELECTRONIC PATIENT MONITOR WITH AUTOMATICALLY CONFIGURED ALARM PARAMETERS

(75) Inventors: Toby E. Smith, Broken Arrow, OK (US); Craig L. Cooper, Inola, OK (US)

(73) Assignee: Bed-Check Corporation, Tulsa, OK (US)

( * ) Notice: Subject to any disclaimer, the term of this patent is extended or adjusted under 35 U.S.C. 154(b) by 0 days.

(21) Appl. No.: 09/944,622

(22) Filed: Aug. 31, 2001

(51) Int. Cl.[7] .......................... G08B 23/00; A61B 5/103
(52) U.S. Cl. .................. 600/595; 340/573.1; 340/573.4
(58) Field of Search ............................... 600/300, 301, 600/587, 595; 340/573.1, 573.4, 573.5, 286.06, 286.07, 666, 667, 310.01, 310.06, 310.07, 552

(56) References Cited

U.S. PATENT DOCUMENTS

| | | |
|---|---|---|
| 3,239,830 A | 3/1966 | Schmitt |
| 3,775,675 A | 11/1973 | Freeze et al. |
| 4,122,660 A | 10/1978 | Canavan |
| 4,134,272 A | 1/1979 | Reimann |
| 4,242,672 A | 12/1980 | Gault |
| 4,788,487 A | 11/1988 | Picklesimer |
| 5,137,033 A | 8/1992 | Norton |
| 5,182,546 A | 1/1993 | Shinbori et al. |
| 5,410,297 A | 4/1995 | Joseph et al. |
| 5,633,627 A | 5/1997 | Newham |
| 5,652,891 A | 7/1997 | Kitamura et al. |
| 5,654,694 A | 8/1997 | Newham |
| 5,682,882 A * | 11/1997 | Lieberman ................... 600/587 |
| 5,738,102 A | 4/1998 | Lemelson |
| 5,751,214 A | 5/1998 | Cowley et al. |
| 5,754,462 A | 5/1998 | Little |
| 5,938,593 A * | 8/1999 | Ouellette ..................... 600/300 |
| 5,945,914 A | 8/1999 | Holmes et al. |
| 6,072,392 A | 6/2000 | Jefferson et al. |
| 6,111,509 A | 8/2000 | Holmes |
| 6,229,430 B1 | 5/2001 | Dewey |
| 6,292,102 B1 | 9/2001 | Smith |
| 6,307,476 B1 | 10/2001 | Smith et al. |

* cited by examiner

Primary Examiner—Eric F. Winakur
Assistant Examiner—David J. McCrosky
(74) Attorney, Agent, or Firm—Fellers, Snider, Blankenship, Bailey & Tippens, P.C.

(57) ABSTRACT

There is provided herein an electronic patient monitor that is suitable for use with a variety of different sensors and which automatically configures itself depending on the sensor that is used and/or the environment in which the electronic monitor is placed. In a first preferred embodiment, the electronic monitor determines whether it is being used on a bed or a chair by sensing whether or not a nurse call connector is present. If such a connector is plugged into the monitor, the unit will assume that it is being used with a sensor that has been placed on a bed and will configure its internal parameters appropriately. Such configuration would include changing a delay time to provide for longer delays before sounding an alarm than would be used with a chair monitor.

26 Claims, 5 Drawing Sheets

ELECTRONIC PATIENT MONITOR WITH AUTOMATICALLY CONFIGURED ALARM PARAMETERS

FIELD OF THE INVENTION

This invention relates generally to monitoring systems and more particularly concerns devices and systems used to monitor seated or lying patients in homes or in medical environments such as hospitals, institutions, and other caregiving environments.

BACKGROUND OF THE INVENTION

It is well documented that the elderly and post-surgical patients are at a heightened risk of falling. These individuals are often afflicted by gait and balance disorders, weakness, dizziness, confusion, visual impairment, and postural hypotension (i.e., a sudden drop in blood pressure that causes dizziness and fainting), all of which are recognized as potential contributors to a fall. Additionally, cognitive and functional impairment, and sedating and psychoactive medications are also well recognized risk factors.

A fall places the patient at risk of various injuries including sprains, fractures, and broken bones—injuries which in some cases can be severe enough to eventually lead to a fatality. Of course, those most susceptible to falls are often those in the poorest general health and least likely to recover quickly from their injuries. In addition to the obvious physiological consequences of fall-related injuries, there are also a variety of adverse economic and legal consequences that include the actual cost of treating the victim and, in some cases, caretaker liability issues.

In the past, it has been commonplace to treat patients that are prone to falling by limiting their mobility through the use of restraints, the underlying theory being that if the patient is not free to move about, he or she will not be as likely to fall. However, research has shown that restraint-based patient treatment strategies are often more harmful than beneficial and should generally be avoided—the emphasis today being on the promotion of mobility rather than immobility. Among the more successful mobility-based strategies for fall prevention include interventions to improve patient strength and functional status, reduction of environmental hazards, and staff identification and monitoring of high-risk hospital patients and nursing home residents.

Of course, direct monitoring of high-risk patients, as effective as that care strategy might appear to be in theory, suffers from the obvious practical disadvantage of requiring additional staff if the monitoring is to be in the form of direct observation. Thus, the trend in patient monitoring has been toward the use of electrical devices to signal changes in a patient's circumstance to a caregiver who might be located either nearby or remotely at a central monitoring facility, such as a nurse's station. The obvious advantage of an electronic monitoring arrangement is that it frees the caregiver to pursue other tasks away from the patient. Additionally, when the monitoring is done at a central facility a single person can monitor multiple patients which can result in decreased staffing requirements.

Generally speaking, electronic monitors work by first sensing an initial status of a patient, and then generating a signal when that status changes, e.g., he or she has sat up in bed, left the bed, risen from a chair, etc., any of which situations could pose a potential cause for concern in the case of an at-risk patient. Electronic bed and chair monitors typically use a pressure sensitive switch in combination with a separate electronic monitor which conventionally contains a microprocessor of some sort. In a common arrangement, a patient's weight resting on a pressure sensitive mat (i.e., a "sensing" mat) completes an electrical circuit, thereby signaling the presence of the patient to the microprocessor. When the weight is removed from the pressure sensitive switch, the electrical circuit is interrupted, which fact is similarly sensed by the microprocessor. The software logic that drives the monitor is typically programmed to respond to the now-opened circuit by triggering some sort of alarm—either electronically (e.g., to the nursing station via a conventional nurse call system) or audibly (via a built-in siren) or both. Additionally, many variations of this arrangement are possible and electronic monitoring devices that track changes in other patient variables (e.g., wetness/enuresis, patient activity/inactivity, etc.) are available for some applications.

General information relating to mats for use in patient monitoring may be found in U.S. Pat. Nos. 4,179,692, 4,295,133, 4,700,180, 5,600,108, 5,633,627, 5,640,145, 5,654,694, and 6,111,509 (concerning electronic monitors generally). Additional information may be found in U.S. Pat. Nos. 4,484,043, 4,565,910, 5,554,835, and 5,623,760 (sensor patents) and U.S. Pat. No. 5,065,727 (holsters for electronic monitors), the disclosures of all of which patents are all incorporated herein by reference. Further, co-pending U.S. patent application Ser. No. 09/285,956, discusses a sensing device which contains a validation circuit incorporated therein, and this application is similarly incorporated herein by reference.

It is well known that the sensing devices that are placed on chairs and beds usually operate in a similar fashion. For example, in the case of pressure sensitive mats, the principal difference between chair and bed mats is the length of the mat, with chair mats usually being shorter. Thus, there would be some economy in developing electronic monitors that can function either as a bed or chair monitor and this has, in fact, been done.

However, the monitor settings in these two environments are different and it falls to the caregiver to adjust the parameters accordingly at the time the switch is made. For example, it is customary in the case of bed sensors to program the electronic monitors to permit brief periods of time "off of the mat" to accommodate those situations where a patient is merely adjusting his or her location in the bed. This, of course, can reduce the incidence of false alarms substantially in a restless patient. This time period, called a "delay time" hereinafter, is usually set to near zero in the case of chair monitors. This is done for many reasons, but among the foremost is that patients that are seated in chairs can arise and place themselves into danger much more quickly than a patient that is lying down because the seated patient is already vertically oriented. As a consequence, it is customary to have relatively short delay times when chair mats are monitored.

Although most electronic monitors will accommodate and can be set to observe a wide range of delay times, it is the responsibility of the caregiver to make certain that the appropriate parameters are adjusted at the time the monitor is reassigned. Failure to do this could possibly place the patient at risk and/or result in false alarms which must be attended to by an increasingly overworked staff.

More generally, it often makes sense economically to design an electronic monitor that can detect the status of a variety of different sensors types such as, for example, pressure sensitive switches, proximity switches, wetness sensors, etc. But, obviously, the particular monitor parameters that should be used might be widely different for an incontinence sensor and a pressure sensitive switch. It should be clear that, where an electronic monitor can be used in a variety of different settings, it would be advantageous to have that monitor automatically configure itself appropriately depending on the particular sensors that it is used with. As a specific example, patient safety would be increased if an electronic patient monitor could automatically reconfigure itself each time it was utilized in a different environment. Currently, the responsibility of changing monitor parameters falls exclusively to the caregiver, who may not know how—or who may forget—to adjust the appropriate parameters. Additionally, even if the caregiver remembers that it is necessary to change a monitor parameter, he or she may make that change imperfectly (e.g., forget to reset the monitor after changing the delay time), thereby leaving the monitor in its original state. All of the foregoing can contribute to an increased risk of a patient rising and falling before the staff can intercept him or her.

Heretofore, as is well known in the patient monitor arts, there has been a need for an invention to address and solve the above-described problems and, more particularly, there has been a need for an electronic patient monitor that would automatically sense its environment and configure itself depending on the particular environment in which it was used. Such an invention would increase patient safety by automatically adjusting a monitor's parameters without fail each time it is repositioned into a new environment. Accordingly, it should now be recognized, as was recognized by the present inventors, that there exists, and has existed for some time, a very real need for a system for monitoring patients that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided an electronic patient monitor that is suitable for use with a variety of different sensors and which automatically configures itself depending on the sensor that is used.

In a first preferred embodiment, the monitor of the instant invention determines whether it is being used on a bed or a chair by sensing whether or not a room nurse call interface is present. In the event that such a connector is plugged into the monitor, the unit will make the assumption that it is being used with a sensors that has been placed on a bed and will configure itself appropriately. On the other hand, if the instant monitor does not detect a nurse call connection, its parameters, including the delay time parameter, will default to those that are appropriate for use in a chair. Preferably, when the monitor is used on a chair the delay time will be automatically set to be near zero, whereas when the monitor is on a bed a delay time of a few seconds will preferably be used.

In another preferred embodiment, the electronic monitor of the instant invention will adjust its operating parameters depending on any number of environmental parameters that might be sensed thereby. As first example example, if the monitor senses that AC power has been supplied (i.e., the unit has been connected to the wall), it will automatically configure itself for use on a bed. In another preferred arrangement, depending on the level of lighting in the room, the volume of the in-unit speaker will be adjusted upward or downward. In other preferred configurations, the in-monitor siren will vary its alarm duration or its alarm sound depending on whether it senses that it has been attached to a bed, chair, wetness, or other type of sensor, According to another preferred embodiment, there is provided an electronic patient monitor which includes a battery backup, so that when the monitor is connected to a wall power supply and, if that power supply fails, it may take action accordingly including, by way of example, sounding a distinctive alarm to signal the sensing of the power outage. Additionally, the preferred embodiment will, for a period of time, keep the nurse call relay closed. This action prevents the sending of an unintended "patient exit" signal to the nurses station, which would normally be the case if the power failed. Additionally, and preferably, the electronic monitor will hold the relay closed until such time as the power returns or until the onboard battery is nearly exhausted, which ever is first. In the event that a low battery condition occurs during a power outage, the preferred response is to send an alarm via the nurse call and/or issue a distinct audible alarm to inform the staff of the problem, for example, a sound such as a "chirp" might be used.

In still another preferred arrangement, the electronic monitor of the instant invention will interrogate a circuit that has been incorporated into the sensor to determine the environment in which it is being used. Then, depending on the results of that interrogation, one or more operating parameters will be adjusted to match the preferred configuration in that environment. For example, the electronic monitor might change its configuration from a normal/open sense (e.g., in this case of a wetness monitor) to normal/closed sense (e.g., a pressure sensitive switch such as a bed mat).

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to apply to all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

According to a preferred aspect of the instant invention, there is provided an electronic monitor for use with a patient sensor, wherein the monitor automatically configures itself depending on the particular sensor that it is used with. This configuration might take many forms, but in a preferred embodiment the monitor delay time will be adjusted depending on the sort of sensors that is attached thereto.

GENERAL BACKGROUND

By way of general background, in a typical arrangement, a pressure-sensing mat of the sort discussed herein is a sealed "sandwich" composed of three layers: two outer layers and an inner (central) layer positioned between the two outer layers. The outer layers are usually made of some sort of plastic and are impermeable to fluids and electrically non-conductive on their outer faces, where "outer" is determined with respect to the middle layer. The inner surface of each of the outer layers—which inner surfaces are oriented to face each other from opposite sides of the central layer—is made to be electrically conductive, usually by printing a conductive (e.g., carbon-based) ink on that surface. The compressible middle "central spacer" is made of a non-conductive material and serves to help keep the two conductive faces apart when a patient is not present on the sensor. The central spacer is discontinuous, which makes it possible for the two conductive inner surfaces to be forced into contact through the one or more discontinuities when weight is applied to the switch. By attaching a separate electrical lead to each of the conductive inner faces, it can readily be determined via a simple continuity (or low voltage) check whether a weight is present on the sensor (e.g., a patient is seated thereon). Removal of the weight causes the central spacer to expand and press apart the two conducting faces, thereby breaking the electrical connection between them. Thus, a device that monitors the resistance across the two electrical leads may determine when a patient has moved from a seated or prone position.

Figure 1:
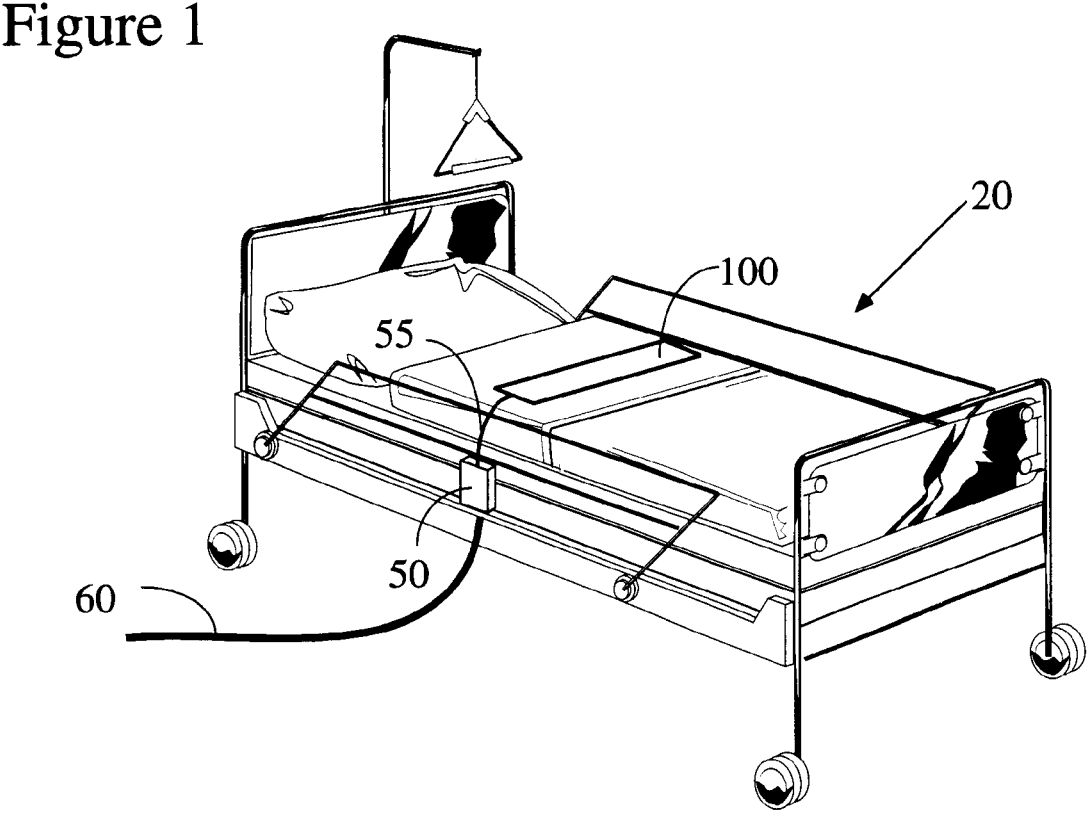
FIG. 1 illustrates the general environment of the instant invention, wherein an electronic patient monitor is connected to a bed mat.

Turning first to FIG. 1 wherein the general environment of the instant invention is illustrated, in a typical arrangement a sensing mat 100 is placed on a hospital bed 20 where it will lie beneath a weight-bearing portion of the reclining patient's body, usually the buttocks and/or shoulders. Generally speaking, the mat 100/monitor 50 combination works as follows. When a patient is placed atop the mat 100, the patient's weight compresses the mat 100 and closes an electrical circuit, which closure is sensed by the attached electronic patient monitor 50. When the patient attempts to leave the bed, weight is removed from the sensing mat 100, thereby breaking the electrical circuit, which interruption is sensed by the attached electronic patient monitor 50. The patient monitor then signals the caregiver per its pre-programmed instructions. In some cases, the signal will amount to an audible alarm or siren that is emitted from the unit. In other cases, an electronic signal could be sent to a remote nurses/caregivers station via electronic line 60. Note that additional electronic connections not pictured in this figure might include a monitor power cord to provide a source of AC power—although, as generally pictured in this figure, the monitor 50 can certainly be configured to be either battery or AC powered.

Figure 2:
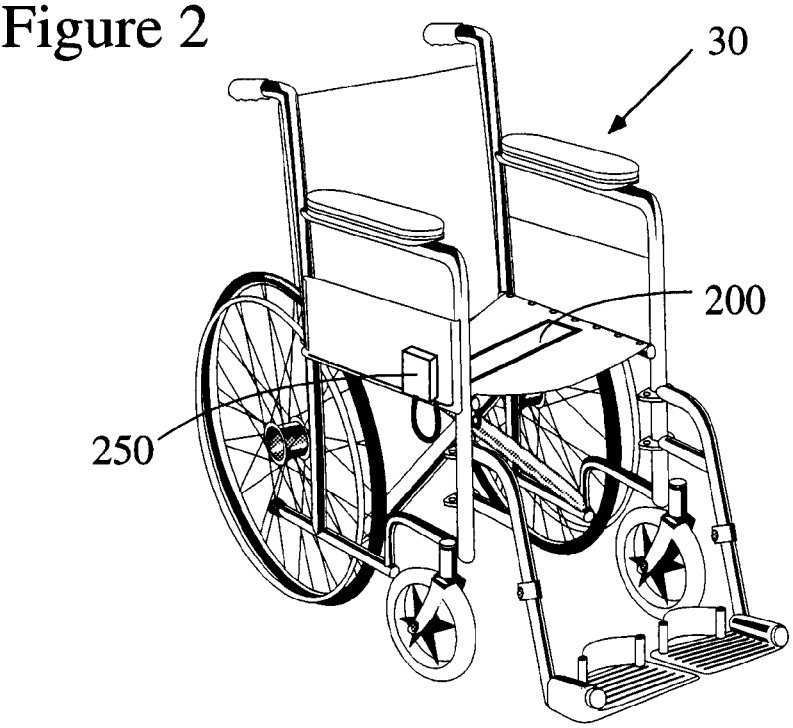
FIG. 2 illustrates the general environment of the instant invention, wherein an electronic patient monitor is connect to a chair mat.

In another common arrangement, and as is illustrated in FIG. 2, a pressure sensitive chair sensor 200 might be placed in the seat of a wheel chair or the like for purposes of monitoring a patient seated therein. As has been described previously, a typical configuration utilizes a pressure sensitive switch 200 which is connected to electronic chair monitor 250 that is attached to the chair 30. Because it is anticipated that the patient so monitored might choose to be at least somewhat mobile, the monitor 250 will usually be battery powered and will signal a chair-exit event via an internal speaker, rather than a nurse-call interface.

Finally, there are many other patient monitor sensors that would be suitable for use with the instant invention including, without limitation, toilet seat monitors (see, e.g., U.S. Pat. No. 5,945,914), wetness monitors (U.S. patent application Ser. No. 09/596,268), decubitus ulcer monitors (U.S. patent application Ser. No. 09/591,887), etc.

It a general practice in this industry to allow the nurse/caregiver to configure the electronic monitors 50 and 250 to wait some specific period of time after an exit event has been sensed before sounding an alarm. This helps reduce the incidence of false alarms where, for example, the bed patient has temporarily shifted positions or has started to rise and then changed his or her mind. (That is, if the monitor senses a return of weight to the mat within the prescribed time period, it will not sound its alarm.) On the other hand, it is a further general practice in this industry to configure monitors used with chair-type sensors with much shorter delays (often with no time delay) than would be used with bed sensors. This is because seated patients can put themselves at risk much quicker than those lying in bed and nurses need to respond more quickly in these situations.

It should be clear that it is advantageous to the caregiver to be able to use the same electronic monitor 50 with both bed 100 and chair 200 sensors. However, to do so requires that the alarm time delay be changed (usually shortened) when it is moved from a bed 20 to a chair 30. Heretofore, it has been the practice in the industry to have to manually reconfigure the electronic monitor when it is moved between applications. This involves, in many cases, changing dip switches or other manual indicators to signal the monitor that its time delay should be altered, followed by a reset or reboot of the unit. Even in those cases where the change is made through the use of pre-assigned buttons on the face of the monitor 50, the nurse or caregiver must still remember to make this change and, in some cases, must remember to reboot thereafter.

PREFERRED ELECTRONIC MONITOR EMBODIMENTS

Figure 3:
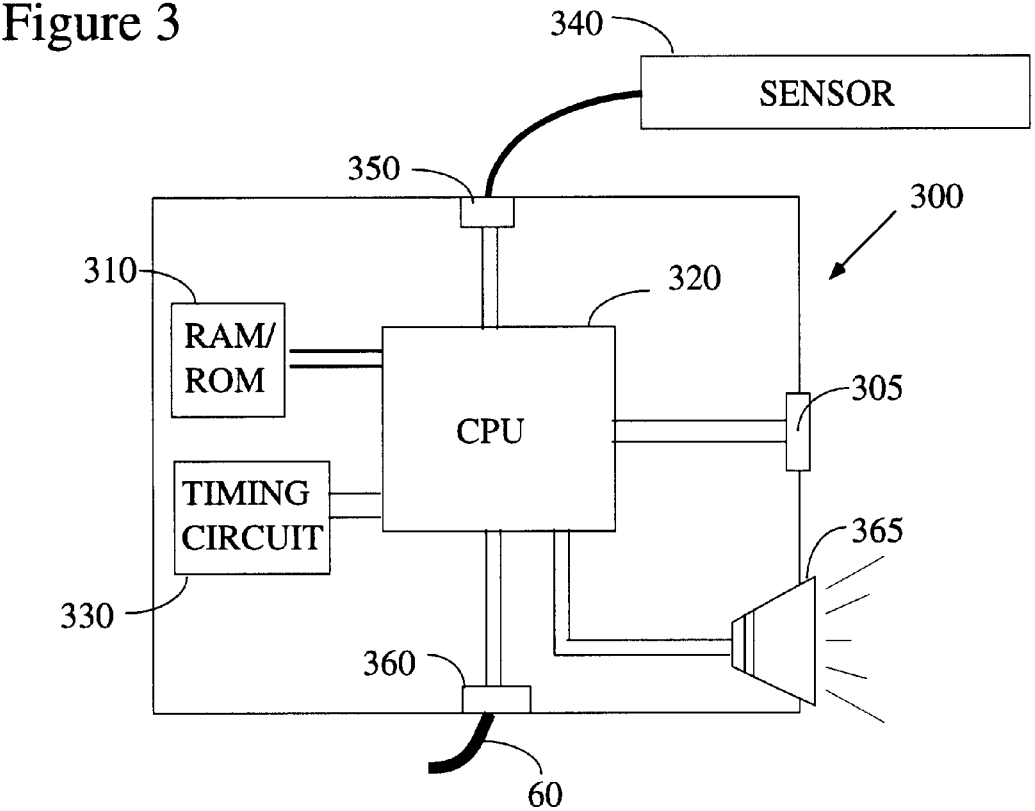
FIG. 3 contains a schematic drawing of a preferred monitor/sensor arrangement.

Turning now to FIG. 3 wherein a first preferred aspect of the instant invention is disclosed in greater detail, at its core the monitor 300 utilizes a microprocessor CPU 320 and some sort of clock chip 330, the purposes of the clock 330 being to allow the CPU 320 to monitor the passage of time at least for purposes of determining a time delay. It should be noted that the clock 330 need not be external to the CPU 320 and, in fact, the CPU 320 itself might function as a clock through the execution of pre-timed loops. Additionally, some amount of RAM/ROM 310 is customarily provided for use by the CPU 320. The ROM component might contain operating instructions (e.g., boot instructions) and default parameters values. The RAM component would be used by the CPU 320 for storage of data values as needed. The RAM might be either volatile or nonvolatile depending on the needs of the electronic monitor 300 designer. All of this is well known to those of ordinary skill in the art.

Power adaptor 305 is designed to allow the monitor 300 to operate with either DC or AC sources. In the preferred embodiment, the instant monitor 300 will be battery powered, thereby making it suitable for use with either beds or chairs. Of course, as used herein the term "battery" should be understood in its broadest sense to include conventional disposable and rechargeable, batteries, as well as fuel cells and other portable power sources.

Nurse call interface output 360 is provided for those circumstances wherein the unit 300 is to be connected to a conventional nurse call system, or other remote signaling arrangement. In more particular, in some cases a connector at the terminus of line 60 will be inserted into interface output 360 so that the monitor can send signals to a remote caregiver and receive signals back from the remote caregiver if that is desired. It will be assumed for purposes only of the instant embodiment that the CPU can sense whether or not such a connection has been offered. Methods of providing the CPU 320 access to such information are well known to those of ordinary skill in the art.

Nurse call interface output 360 is provided to allow the microprocessor 320 to send a signal to a remote receiver such as a nurses station, if that is needed. In the preferred embodiment, a connecting wire 60 will connect the monitor 300 to the nurse call network, which is conventionally accessed by way a wall-plug. Of course, it is envisioned that an alarm might also be sounded locally (e.g., from an audio speaker 365 that is preferably built into the monitor) in addition to (or instead of) notifying the nurses station. When the monitor 300 is placed on a wheel chair, a local alarm may be the most practical solution. For purposes of the instant disclosure, the term "alarm" will be used in its broadest sense to refer to a local or remote speaker, flashing light, pulsating signal (e.g., of the sort used in conventional pagers) or similar signaling mechanisms which are responsive to commands from the CPU 320 and which can be used to obtain the attention of a caregiver. Of course, a "speaker" includes, without limitation, piezoelectric or other devices capable of generating an audible alarm signal. Thus, when the term "speaker" is used hereinafter, that term should be construed in the broadest possible sense to include any device capable of emitting an audible alarm signal under the control of the microprocessor 320. Additionally, when speaker is used herein that term should also be taken to include an associated power amplifier to drive it, if one is necessary (as it often will be). Finally, it should also be noted that it is not an essential element of the instant invention that the speaker 365 be found within the body of the monitor. The speaker 365 could also be mounted externally thereto, and, as an extreme example, might by located in an adjacent hallway or at the nurses station or anywhere else, provided that it is in electrical communication with the monitor 300

Additionally, the connecting wire 60 might be used to place the CPU 320 into electronic communication with any number of other remote devices, including remote networks, computers, etc. Alternatively, it is known in the art to provide the electronic monitor 300 with additional communications hardware including, for example, a serial port, a parallel port, a USB port, a fire wire port, an infrared communications port, an RF port, etc., all of which would preferably be accessible by the microprocessor 320.

Connected to the monitor 300 is some sort of patient sensor 340, which is preferably a pressure sensitive switch 100 or 200 of the sort discussed previously. That being said, there are many other types of patient monitors that would be suitable for use with the instant invention and a pressure sensitive mat has been selected for the discussion herein only for purposes of specificity and not out of any intent to so-limit the invention to that one sensor.

Figure 5:
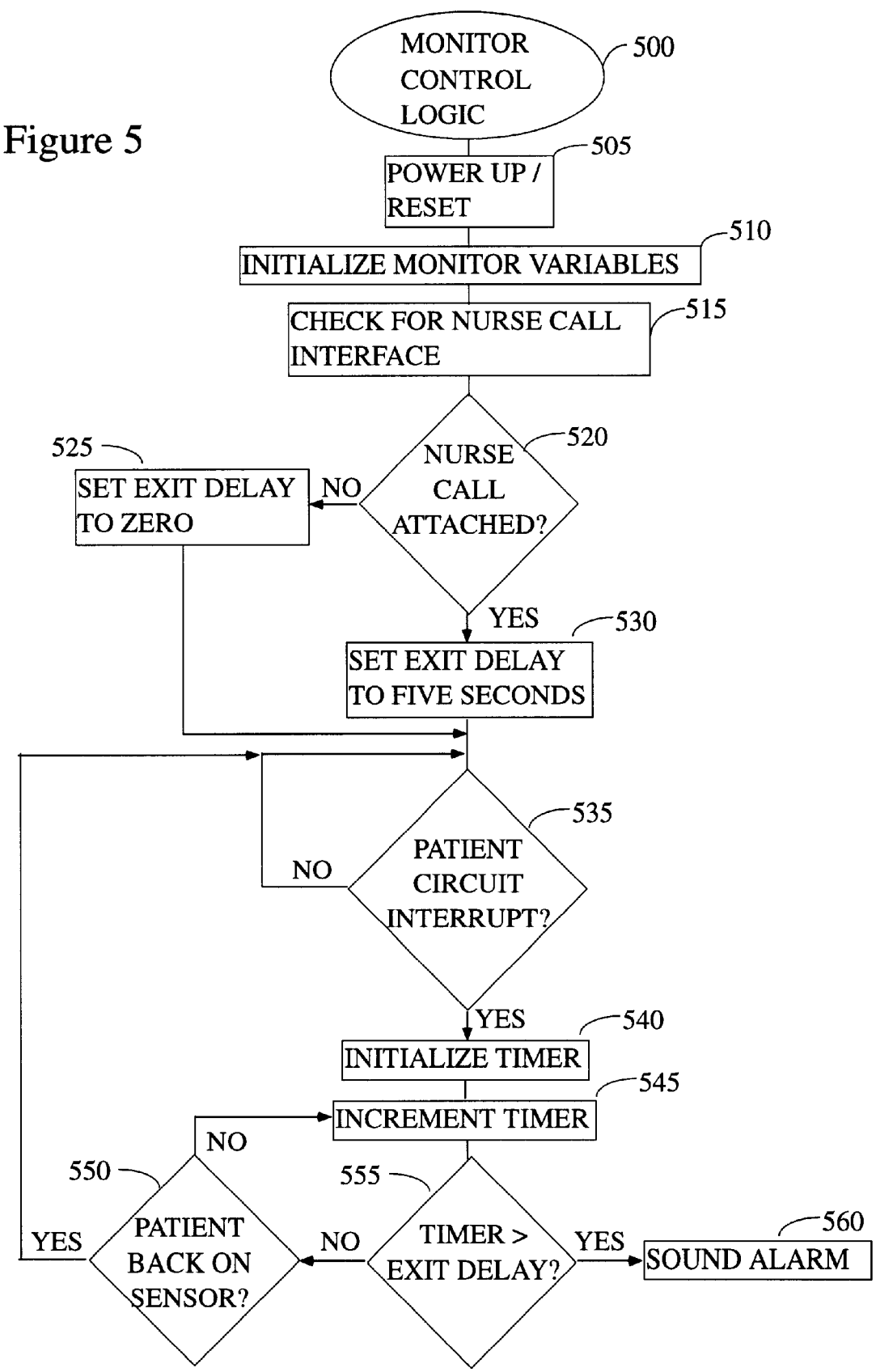
FIG. 5 is a flow chart that illustrates a preferred logic for use with the electronic patient monitor.

In practice, a preferred monitor embodiment 300 would operate as follows. As is generally illustrated in FIG. 5, monitor control logic 500 is preferably stored in ROM and executed when the monitor 300 is powered-up or reset. As a first preferred step, the monitor would initialize its internal variables 510 and do an integrity check of its hardware, etc. Next, a determination 520 will be made as to whether a nurse call cable is attached to the unit. In the event that a nurse call cable is not so attached, the unit will preferably set the exit delay 525 to some small value, e.g., zero seconds. In the alternative, the exit delay will be set to some other value, for example three seconds 530.

Given the value of the exit delay, the preferred monitor control logic 500 continues to monitor the patient detection circuit 535 for evidence of a patient's departure. When the monitor 300 is used with a pressure sensitive switch, the patient's departure is sensed in the form of an interrupt in the patient circuit, which departure would result in the initialization of a timer 540. The monitor 300 would then preferably loop through steps 545, 555, and 550 until one of two events happen. If the patient returns to the sensor before the timer reaches the value set to exit delay (step 550), no alarm will be sounded and the electronic monitor 300 will continue to watch the patient. On the other hand, if the patient does not return to the sensor before the exit delay period has expired, that fact will be noted by sounding an alarm 560, preferably both at the unit 300 itself and, remotely, at the nurse station if the connector is in place.

Of course, there are many operating parameters that might be modified depending on the current state of the patient environment and, more particularly, depending on whether or not the monitor 450 (FIG. 4) is in electronic communication with a nurses station. By way of a further examples, in one preferred arrangement, the patient monitor 450 alarm volume from its speaker 665 (FIG. 6) will be increased when the unit is not connected to a nurses call network. Additionally, the character of alarm that is sounded (e.g., beep, warble, continuous tone, etc.) might be varied depending on whether the nurse station is reachable by the monitor 450, thereby communicating to a caregiver within audible or electronic range whether additional help might be expected. The same information might also be sounded at the time the monitor 450 is first placed into contact with the patient sensor 400, as a verification that the nurse connector is properly inserted. The variations on this theme are countless.

Figure 4:
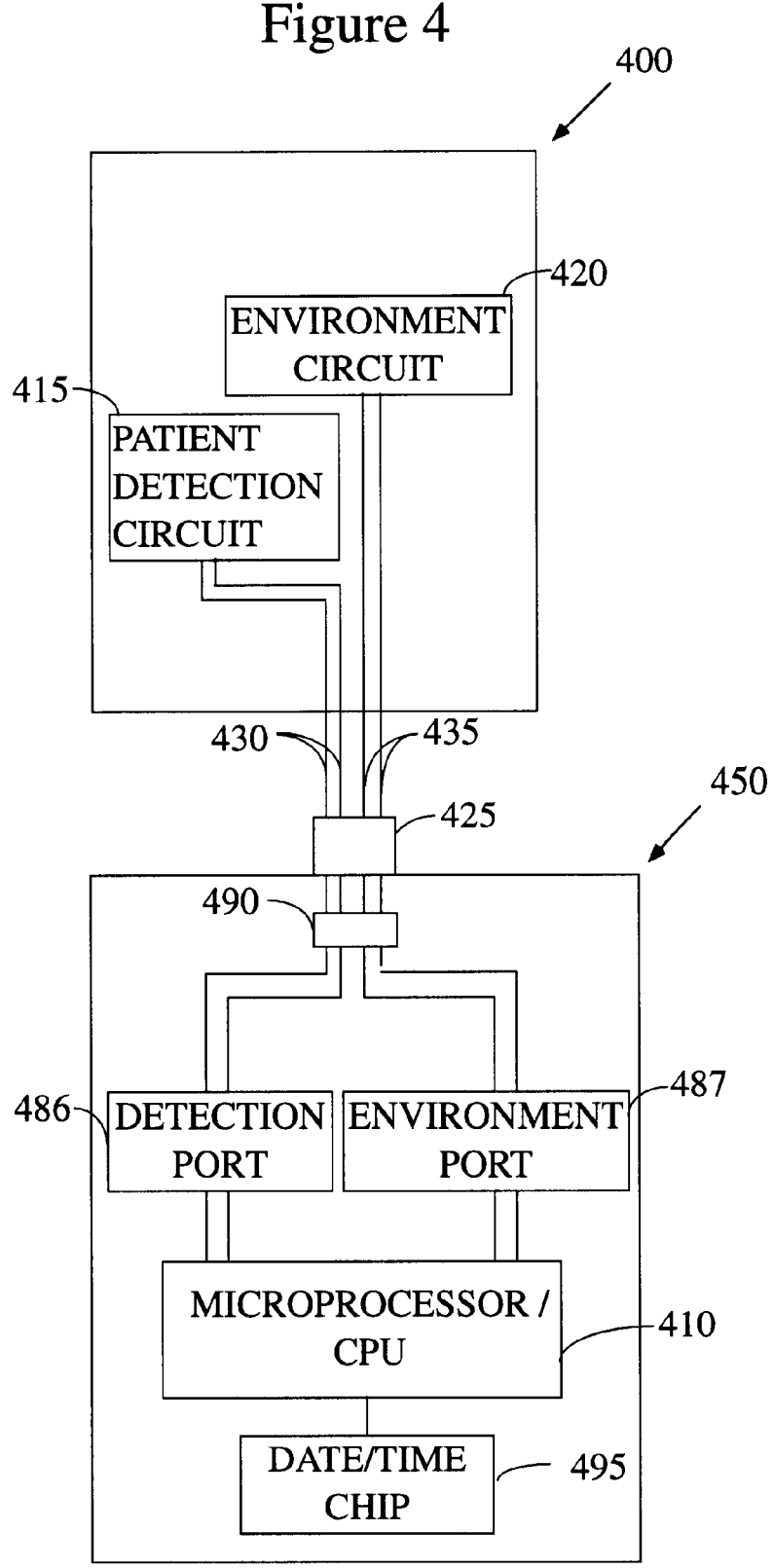
FIG. 4 is a schematic illustration of a preferred monitor embodiment that is in electronic communication with a mat having an environmental circuit associated therewith.

Turning now to another preferred embodiment of the instant invention, and as is illustrated in FIG. 4, there is provided an electronic patient monitor 450 that is designed to be used with a sensor 400 which contains an environmental circuit 420 associated therewith, in addition to the traditional patient detection circuit 415. The preferred electronic patient monitor 450 includes a microprocessor 410, which microprocessor controls the sensing and response of the monitor 450 to changes in the patient detection circuit 415. As was explained previously, the patient detection circuit 415 preferably consists of an electronic circuit that changes states when a patient's weight is placed upon the mat 400, e.g. it might change from an "open" circuit to a "closed" circuit or vice versa. More generally, and as is described in greater detail below, this circuit might be continuously responsive to any other patient condition such as patient activity, wetness, incontinence, etc.

In a preferred embodiment the sensor 400 and monitor 450 are interconnected by a single RJ-11 type electrical connector 425 through which pass four electrical lines: one pair 430 in electrical communication with the patient detection circuit 415 and the other pair 435 in electrical communication with the environmental circuit 420. Note that this is just a preferred embodiment and that other arrangements might include more than four electrical lines (or fewer) and it is well within the ability of one skilled in the art to devise such alternative arrangements. Additionally, connector 425 could be separated into two separate connectors without changing the spirit of the instant invention and it would be well within the ability of one skilled in the art to modify the monitor 450 accordingly.

Microprocessor 410 reads electrical lines 430 through detection port 486 and responds to changes in that circuit according to its pre-programmed instructions. Preferably, the microprocessor 410 will be programmed to query the environmental circuit 420 and, based on the information obtained thereby, modify one or more of its internal program parameters to make the monitor 450 more compatible with the particular sensor attached thereto. It should be clear to those of ordinary skill in the art that the environmental circuit 420 that has been incorporated into sensor 400 could, for example, take the form of a precision resistor, with different resistance values being pre-selected to correspond to different types of sensors (e.g., a 100 ohm resister indicating that a pressure sensitive bed mat was attached thereto). In other preferred embodiments, the environmental circuit 420 could be a capacitor an inductor, or some combination of one or more of each component. As a further example of the sort of circuit 420 that would be appropriate for use with the instant invention, the inventors contemplate that it could prove to be useful in some applications to install a ROM chip, or even a flash RAM chip, within the sensor 400 as part of the environmental circuit 420. The ROM chip could contain and dispense a wide variety of binary information including, by way of example, a sensor type and serial number, a manufacture date/lot number, and various other parameters that would define the sorts of uses to which the sensor 400 might be put. Flash RAM, on the other hand, could contain all of the foregoing and, additionally, values that might be modified by the monitor 450. In either case, information that is stored within the environmental circuit 420 will be used to configure various parameters within the monitor 450.

The information provided by the environmental circuit 420 might be used in many ways. As a first example, a preferred embodiment of the instant monitor 450 will access the environmental circuit 420 in order to determine whether the attached sensor/switch 400 is a bed mat or a chair mat and, in the event that the sensor 400 is a chair mat, the exit delay for the electronic monitor 450 would preferably be set to some small value (e.g., zero seconds) as has been described previously. By way of example, the environmental circuit 420 might take the form of a simple continuity check to determine whether or not a nurse call connector is inserted into interface 360, such an insertion tending to indicate that the monitor 450 is being used on a bed.

Figure 7:
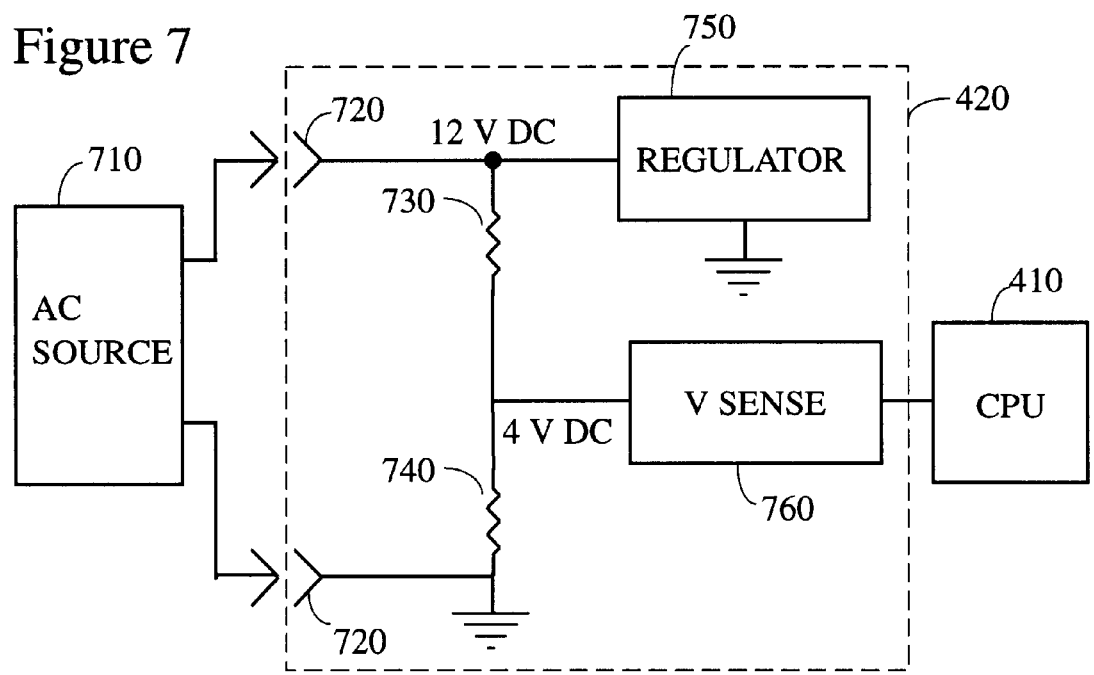
FIG. 7 illustrates a preferred environmental sensor that is suitable for use with the instant invention.

In another preferred arrangement, and as is illustrated in FIG. 7, the environmental sensor 420 is an electronic circuit that is designed to use the connection to an AC power source 710 as an indicator of whether the monitor 450 is attached to a bed or a chair. As can be seen in FIG. 7, in a preferred embodiment one pin of the CPU 410 will be in electric communication with the simple circuit which consists of resistors 730 and 740, regulator 750 and Vsense element 760. In this particular example, when an active AC power source 710 is mated with the monitor 450 through connectors 720, then Vsense will be greater than a logic "1" and the monitor software will change the exist delay time to a longer value, e.g., three seconds. On the other hand, if the Vsense is less than 1, as it will be if the monitor 450 is not connected to AC power, in the preferred arrangement the monitor software will note that fact and set the exit delay to a "chair exit delay" value (i.e., one nearer to zero).

As still another example, if the monitor 450 determines that the attached sensor 400 is a wetness sensor, the monitor 450 would typically be programmed to change its configuration to sound an alarm immediately upon detection of a closed sensor circuit (i.e., if urine, blood, vomit, or another fluid has completed the sensor circuit), in contrast to the usual case with a bed mat, wherein an alarm is generated upon the detection of an open circuit (i.e., the patient has risen).

In another preferred arrangement, the environmental circuit 420 will be an internally located thermometer which measures the temperature of the sensor 400. Temperature information might be useful medically (e.g., to detect the body temperature of the patient), however for purposes of the instant invention the temperature of the sensor 400 can be used to determine whether or not it has been moved from its location proximate to the patient's body. For example, a patient may have moved a wetness sensor to an alternative location so as to avoid embarrassment, etc.

As illustrated in FIG. 4, the environmental circuit 420 is preferably made a part of—and incorporated within—the sensor 400. However, it is anticipated by the instant inventor that the environmental circuit 420 could be incorporated within the RJ-11-type connector 425 for some applications or even designed to be a separate module which is positioned between the sensor 400 and the monitor 450. In any case, the physical location of the environmental circuit 420 is material to the instant application, except that its functionality may vary somewhat depending upon where it is positioned with respect to the sensor 400.

Figure 6:
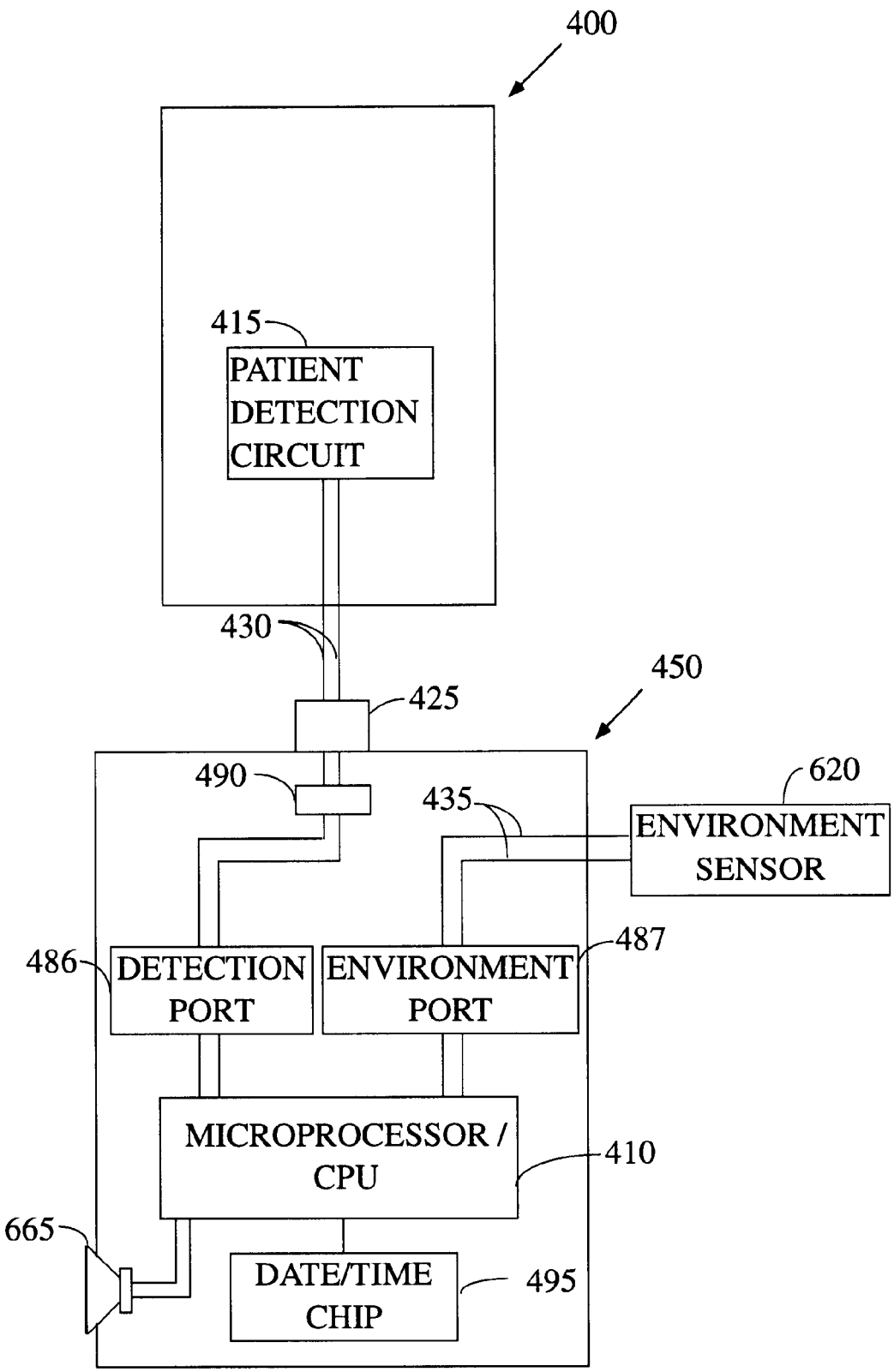
FIG. 6 contains a schematic illustration of a preferred monitor/sensor arrangement, wherein the environmental circuit is separate from the sensor.

In still another preferred arrangement, and as is generally illustrated in FIG. 6, input from an environmental sensor 620—which environmental sensor 620 is separate from the patient sensor 400—can similarly be used to automatically configure various parameters with the monitor 450. By way of example, environmental sensor 620 might be an ambient light sensor, a thermometer, a microphone, etc. each of which would provide information that would enable the monitor 450 to configure its operative parameters more effectively.

According to a first preferred embodiment, environmental sensor 620 is a photosensitive element such as a photovoltaic device, a photodiode, a phototransistor, a photo resister, a CCD camera, a digital camera or any other electronic circuit that is responsive to ambient light. Preferably, information about the presence or absence of ambient light (or the amount of light sensed or its frequency) in the vicinity of the sensor will be used to configure parameters such as speaker 665 volume (e.g., higher volume levels would be used when the sensor 620 detects light and lower levels at night). Of course, an alternative arrangement would be to adjust the speaker 665 volume upward if the sensor detected a low light level and the clock indicated that it was during the day, which might occur if the monitor 450 were covered by bedding. Note that in still another arrangement, the speaker volume might also be decreased/increased based on the current clock 495 time, with times corresponding to "night" being assigned a lower speaker volume. Similarly, the exit delay might be lengthened at night to account for the fact that many patients are restless in their sleep and periodically adjust their position in bed, thereby briefly removing their weight from the pressure sensitive mat that has been placed beneath them. Needless to say, there are many variations of this theme that could be devised by one of ordinary skill in the art.

According to another preferred arrangement, environmental sensor 620 is a thermometer which would preferably measure the ambient/room temperature near the monitor 450. This information might be useful for many purposes, among which are early detection of room fires, etc. In the even that the monitor 450 senses excessive levels of heat, it would normally be programmed to issue an audible alarm via speaker 665, as well as notify the remote nurses station.

According to still another preferred embodiment, the environmental sensor 620 takes the form of a microphone or similar device for measuring the ambient level of sound proximate to the monitor 450. In a preferred arrangement, the volume of speaker 665 will be increased or decreased to compensate for changes in the ambient sound level, thereby increasing the probability that the alarm will be heard locally. Finally, in some applications it might be beneficial to monitor, say, a patient's presence via a pressure sensitive switch, while simultaneously "listening" for trigger words such as "help", "nurse", or, more generally, for any particular word or for a loud/atypical sound such as, for example, sounds associated with breaking glass or an object falling.

Finally, those of ordinary skill in the art will recognize that it might be necessary to filter the response to the environmental sensor 620, so as to reduce the risk of false alarms. For example, where the environmental sensor 450 is designed to respond to sound, a threshold would typically be established so that the alarm would only be generated for truly atypical events, rather than for common sounds such as people talking, doors shutting, etc. Thus, the caregiver will usually be provided with the ability to define a set point so to which the sensed value of the sensed environmental variable will be compared. In such a case, an alarm would only be triggered if the sensed environmental variable crossed (i.e., either exceeded or dropped below, depending on the value sensed) the user-defined set point.

CONCLUSIONS

Although the preferred embodiment of the instant invention is designed to be used with an electronic patient monitor containing a microprocessor, that is not an essential element of the instant invention and it is certainly possible and within the ability of one of ordinary skill in the art to construct a simple analog patient monitor that is responsive to the patient detection circuit and environmental circuits, but which does not contain a microprocessor. Thus, when the term "electronic patient monitor" is used herein, that term should be interpreted in its broadest sense to include both patient monitors that have—and those that do not have—controlling microprocessors.

When the term microprocessor is used herein, it should be understood in its broadest sense to include any programmable device that is capable of recognizing signals from a patient sensor, setting internal parameter values based on external information, and responding to patient activity in accordance with the parameter values so set. These sorts of modest requirements may be satisfied by any number of programmable logic devices ("PLD") including, without limitation, gate arrays, FPGA's (i.e., field programmable gate arrays), CPLD's, EPLD's, SPLD's, PAL's, FPLA's, FPLS, GAL, PLA, FPAA, PSoC, SoC, CSoC, etc., as those acronyms and their associated devices are known and used in the art. Further, many devices contain microprocessors integral thereto, e.g., micro controllers, and the instant disclosure is intended to encompass those sorts of devices as well.

Further, when the term "time circuit" is used herein, it should be understood in its broadest sense to include, not only a traditional time chip which is separate from the microprocessor, but also any sort of timer that is implemented within the microprocessor in software or otherwise. Thus, "timing circuit" should include both hardware and software timers. It should further be understood to include timing that has been synthesized from the AC power line or otherwise.

Still further, it should be noted and remembered that the preferred electronic monitor includes programming instructions stored therein for execution by the microprocessor, which programming instructions define the monitor's response to the patient and environmental sensors. Although ROM is the preferred apparatus for storing such instructions, static or dynamic RAM, flash RAM, EPROM, PROM, or any similar volatile or nonvolatile computer memory could be used. Further, it is not absolutely essential that the software be permanently resident within the monitor, although that is certainly preferred. It is possible that the operating software could be stored, by way of example, on a floppy disk, a magnetic disk, a magnetic tape, a magneto-optical disk, an optical disk, a CD-ROM, flash RAM card, a ROM card, a DVD disk, or loaded into the monitor over a network as needed. Thus, "program memory" as that term is used herein should be interpreted in its broadest sense to include the variations listed above, as well as others.

Even further, the term "environmental sensor" is intended to be broadly applied to any electronic circuit that provides information different from that which is collected by the patient sensor. That is, the central focus of the instant invention is how ancillary information may be used by a patient monitor to automatically modify its response when a change is sensed in a patient's state. The circumstances under which an alarm is generated (e.g., patient absence, wetness, incontinence, temperature, etc.), and/or the character of that alarm, (e.g., loud, soft, short, long, etc.) are automatically adjusted based on the value of some separately measured environmental variable or variables (e.g., whether the monitor is connected to bed or chair, connected to nurse station or not, whether the patient's room is light or dark, etc.). Thus, an environmental sensor might be as simple a circuit that allows the patient monitor to determine whether or not it is plugged into a nurse call system, or whether or not the monitor is attached to AC power. In other situations, the environmental sensor might be configured to look outside of the monitor/sensor combination and could take the form of photosensitive elements, thermometers, etc., that measure ambient conditions within the patient's room and in the patient's vicinity. In still other preferred arrangements, the "environmental sensor" might actually measure a plurality of different environmental variables, with the information so collected being utilized by the patient monitor to set one or more internal programming parameters and/or trigger alarm conditions. As a consequence, when the term "environmental sensor" is used herein, it should be broadly interpreted to include any electrical circuit that is suitable for accomplishing the above-described focus of the instant invention.

Additionally, it should be noted that, although the instant patient monitor is designed to automatically modify its operating parameters based on input from an environmental sensor, it might possibly be the case that the caregiver and/or the microprocessor, would want to override the default parameter value. For example, if a caregiver wishes to monitor a seated patient via the nurse call system, he or she would want to be able to override the general rule that connection to a nurse call system implies that the patient monitor is connected to a bed and, hence, that a longer alarm delay should be used. Instead, the caregiver would want to be able select a short (or zero) alarm delay time, in contravention to the default value and such a capability would generally be provided. Additionally, it is possible that multiple environmental sensors might be useful in some cases. For example, the monitor might check to see whether it is connected to a nurse call and whether it is connected to AC power in order to help confirm whether it has been attached to a bed or a chair. Similarly, other combinations are possible and have been specifically contemplated by the instant inventors.

In still another arrangement, multiple patient sensors might be used, with each such sensor being designed to detect a different condition of the patient and with all sensors being monitored by a single CPU. As an example, a bed-exit sensor might be used in combination with an enuresis sensor, with both sensors being attached to the same electronic monitor. Further, in such an arrangement, the monitor could be programmed to respond differently depending on whether one or both of the conditions sensed were in an "alarm" state at any one point in time. For example, different types of audio alarms could be used to differentiate a "bed exit" from a "wet" state. Further, a different sort of alarm, e.g., a different siren, could be used if both conditions were sensed simultaneously, i.e., if wetness were detected and the patient exited the bed. Still further, if the patient were to sit/lay down again, the siren might shift back to the "wetness only" alarm, depending on the preferences of the caregiver. Those of ordinary skill in the art will recognize that many variations on this theme are possible.

Still further, it should be noted that although it is customary to include a microprocessor as part of the electronic patient monitor, in some circumstances the patient sensor or the environmental sensor might additionally contain its own microprocessor. Thus, in the claims that follow, when a microprocessor is called for as part of the electronic patient monitor, that use should not be interpreted as excluding the presence of a microprocessor elsewhere in the system and, in fact, that possibility is specifically contemplated by the instant inventors. Additionally, when the instant application speaks of communication between the microprocessor 410 and the patient sensor 415 (or the environmental sensor 420 or 620), that sort of communication should be interpreted broadly so as to include communication between the microprocessor 410 and another microprocessor that is located in the sensor, the function of which is might be to monitor/control the operation of the sensor.

Finally, it should be noted that the term "nurse call" as that term has been used herein should be interpreted to mean, not only traditional wire-based nurse call units, but more also any system for notifying a remote caregiver of the state of a patient, whether that system is wire based or wireless. Additionally, it should be clear to those of ordinary skill in the art that it may or may not be a "nurse" that monitors a patient remotely and, as such, nurse should be broadly interpreted to include any sort of caregiver, including, for example, untrained family members and friends that might be signaled by such a system.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. An electronic patient monitor for detecting a state of a patient and for generating an alarm in response to a change in the state of the patient, wherein said generated alarm has at least one modifiable operating parameter associated therewith, comprising:
    (a) a patient sensor, said patient sensor positionable to be placed proximate to the patient and responsive to the state of the patient;
    (b) an environmental sensor, said environmental sensor at least for sensing at least one value of an environmental quantity;
    (c) program memory, said program memory at least containing a plurality of computer instructions stored therein;
    (d) a speaker at least for sounding said generated alarm in response to the change in the state of said patient; and,
    (e) a microprocessor in electronic communication with said patient sensor, with said environmental sensor, with said speaker, and with said program memory, said microprocessor for executing said plurality of computer instructions and for responding to said patient sensor and said environmental sensor at least according to said computer instructions, wherein said plurality of computer instructions at least include
        (d1) a first plurality of computer instructions for obtaining from said environmental sensor a value representative of said at least one environmental quantity,
        (d2) a second plurality of computer instructions for automatically modifying said at least one modifiable alarm operating parameter according to said obtained value representative of said at least one environmental quantity,
        (d3) a third plurality of computer instructions for monitoring said patient sensor to detect said change in the state of the patient, and,
        (d4) a fourth plurality of computer instructions for initiating said alarm at least according to said modifiable alarm operating parameter through said speaker upon the detection of said change in the state of the patient.

2. An electronic patient monitor according to claim 1, wherein said environmental sensor is integral to said patient sensor.

3. An electronic patient monitor according to claim 1, wherein said patient sensor is a pressure sensitive mat.

4. An electronic patient monitor according to claim 3,
wherein said environmental sensor is for determining whether said electronic patient monitor is in electrical communication with a nurses station, and
wherein said environmental quantity is representative of whether said electronic patient monitor is in electrical communication with the nurses station.

5. An electronic patient monitor according to claim 4, wherein at least one of said at least one modifiable operating parameters is an exit delay time and wherein said plurality of computer instructions at least include instructions that change said exit delay time depending on whether said electronic patient monitor is in electrical communication with the nurses station.

6. An electric patient monitor according to claim 5, wherein said second plurality of computer instructions at least include instructions that automatically increase said exit delay time depending on whether said electronic patient monitor is in electrical communication with the nurses station.

7. An electronic patient monitor according to claim 1, wherein said environmental quantity is representative of ambient light near the patient and wherein said environmental sensor is selected from a group consisting of a photovoltaic circuit, a photodiode, a phototransistor, a photo resistor, a CCD camera and a digital camera.

8. An electronic patient monitor according to claim 1, wherein at least one of said at least one modifiable operating parameters is an alarm volume and wherein said computer instructions at least include instructions that change said alarm volume depending on said value of said environmental quantity.

9. An electronic patient monitor according to claim 1, wherein said environmental sensor is chosen from a group consisting of a clock circuit, a real-time clock, and a date/time chip.

10. A method of monitoring a state of a patient, wherein is provided the apparatus of claim 1, comprising the steps of:
(a) determining from said patient sensor an initial state of the patient;
(b) determining from said environmental sensor an environmental value representative of a state of the patient environment;
(c) automatically determining a value of at least one of said at least one modifiable alarm operating parameters based at least on least said value representative of the state of the patient environment;
(d) determining a current state of the patient from said patient sensor;
(e) repeating step (d) until said current state of the patient is different from said initial state of the patient;
(f) determining whether to signal an alarm depending at least on said current state of the patient; and,
(g) signaling an alarm condition using at least said speaker if it is so determined in step (f), wherein said signaled alarm condition is according to the determined value of said modifiable alarm operating parameter.

11. A method of monitoring a state of a patient according to claim 10, wherein step (e) comprises:
(e1) repeating steps (b) and (d) until either said current state of the patient is different from said initial state of the patient or until said state of the patient environment changes, and, wherein step (f) comprises:
(f1) determining whether to signal an alarm depending at least on said current state of the patient and said environmental value representative of the state of the patient environment.

12. A method of monitoring a state of a patient according to claim 11, wherein is provided a user defined set point associated with said environmental quantity, step (f) comprises:
(f1) determining whether to signal an alarm depending on at least said current state of the patient, said environmental value representative of the state of the patient environment, and said set point.

13. An electronic patient monitor according to claim 1, wherein said modifiable operating parameters are selected from a group consisting of an exit delay time, an alarm volume, and an alarm type.

14. A method of monitoring a state of a patient using an electronic patient monitor, comprising the steps of:
(a) determining from a patient sensor an initial state of the patient;
(b) determining from an environmental sensor a state of the patient environment;
(c) automatically setting an alarm parameter value based at least on said patient environment state;
(d) determining a current state of the patient from said patient sensor;
(e) repeating step (d) until said current state of the patient is different from said initial state of the patient;
(f) determining whether to signal an alarm depending at least on said current state of the patient; and,
(g) signaling an alarm according to said alarm parameter value if it is so determined in step (f).

15. A method of monitoring a state of a patient using an electronic patient monitor according to claim 14, wherein said environmental sensor of step (b) is an electrical circuit for determining whether said electronic patient monitor is in electrical communication with a nurses station.

16. A method of monitoring a state of a patient using an electronic patient monitor according to claim 15, wherein step (c) comprises the step of:
(c1) determining an exit delay time based at least on whether said electronic patient monitor is in electrical communication with the nurses station, and,
wherein step (f) comprises the steps of:
(f1) determining a length of time since said current state of the patient differed from said initial state of the patient, and,
(f2) sounding an alarm if said determined length of time is greater than said exit delay time.

17. A method of monitoring a state of a patient according to claim 14, wherein step (e) comprises:
(e1) repeating steps (b) and (d) until either said current state of the patient is different from said initial state of the patient or until said state of the patient environment changes.

18. A method of continuously monitoring a state of a patient, comprising the steps of:
(a) providing a patient sensor proximate to the patient, said patient sensor being responsive to the state of the patient;
(b) providing an electronic patient monitor in electrical communication with said patient sensor;
(c) determining an initial state of the patient using said electronic patient monitor and said patient sensor;

(d) providing an environmental sensor proximate to the patient, said environmental sensor measuring an environmental quantity different from the state of the patient and said environmental sensor being in electrical communication with said electronic patient monitor;

(e) using said electronic patient monitor and said environmental sensor to determine a state of the patient environment;

(f) automatically setting at least one alarm response parameter value based on at least said state of the patient environment;

(g) determining a current state of the patient from said patient sensor;

(h) repeating step (g) until said current state of the patient is different from said initial state of the patient; and, (i) automatically sounding an alarm, depending at least on any alarm response parameter values so set, if said current state of the patient is different from said initial state of the patient.

19. A method according to claim 18, wherein said environmental sensor measures a plurality of environmental quantities different from the state of the patient.

20. A method according to claim 18, wherein said environmental sensor is for determining whether said electronic patient monitor is in electrical communication with an AC power source, and, wherein exit delay time is a response parameter, and wherein step (f) comprises the steps of:

(f1) choosing a value for said exit delay time depending on whether said electronic patient monitor is in electrical communication with an AC power source.

21. A method according to claim 20, wherein said exit delay time value is set to a value approximately equal to zero if said electronic patient monitor is not in electrical communication with an AC power source.

22. An electronic patient monitor, comprising:

(a) a patient sensor, said patient sensor positionable to be placed proximate to the patient and responsive to a state of the patient;

(b) an electronic sensor, said sensor at least for determining whether said monitor is in electrical communication with a nurses station or with an AC power source;

(c) program memory, said program memory containing a plurality of computer instructions stored therein, wherein (c1) said computer instructions define at least a portion of said alarm response of said electronic patient monitor to the state of the patient, (c2) said computer instructions include at least one modifiable alarm parameter value which defines at least a portion of said patient monitor alarm response to the state of the patient, and, (c3) at least a portion of said instructions are for automatically modifying at least one of said at least one modifiable alarm parameter values according to whether said patient monitor is in electrical communication with the nurses station or with the AC power source;

(d) a microprocessor in electronic communication with said patient sensor, with said environmental sensor, and with said program memory, said microprocessor at least for executing said computer instructions and for responding to said patient sensor at least according to said computer instructions and said value of said at least one modifiable alarm parameter values; and, (e) a speaker in electronic communication with said microprocessor and responsive thereto, said speaker at least for signaling a change in the state of said patient.

23. An apparatus according to claim 22, wherein said patient sensor is selected from a group consisting of a pressure sensitive bed mat, a pressure sensitive chair mat, a wetness sensor, an incontinence sensor, and a proximity switch.

24. An apparatus according to claim 22, wherein at least one of said at least one modifiable parameter values is an exit delay time.

25. An apparatus according to claim 22, wherein at least one of said at least one modifiable parameter values is an alarm siren type.

26. An apparatus according to claim 22, wherein at least one of said at least one modifiable parameters values is an alarm volume.

* * * * *